(12) United States Patent
Moszner et al.

(10) Patent No.: US 10,512,593 B2
(45) Date of Patent: Dec. 24, 2019

(54) DENTAL MATERIALS BASED ON MONOFUNCTIONAL VINYLCYCLOPROPANE DERIVATIVES

(71) Applicant: Ivoclar Vivadent AG

(72) Inventors: Norbert Moszner, Mauren (LI); Yohann Catel, Buchs (CH); Urs Karl Fischer, Arbon (CH); Sven Tauscher, Buchs (CH)

(73) Assignee: Ivoclar Vivadent AG, Schaan (LI)

( * ) Notice: Subject to any disclaimer, the term of this patent is extended or adjusted under 35 U.S.C. 154(b) by 7 days.

(21) Appl. No.: 15/661,359

(22) Filed: Jul. 27, 2017

(65) Prior Publication Data

US 2018/0036209 A1 Feb. 8, 2018

(30) Foreign Application Priority Data

Aug. 3, 2016 (DE) .................. 10 2016 214 389

(51) Int. Cl.
*A61K 6/083* (2006.01)
*A61K 6/08* (2006.01)
(Continued)

(52) U.S. Cl.
CPC .......... *A61K 6/083* (2013.01); *A61K 6/0023* (2013.01); *A61K 6/0052* (2013.01);
(Continued)

(58) Field of Classification Search
USPC .............. 523/115, 116, 117, 118; 433/228.1
See application file for complete search history.

(56) References Cited

U.S. PATENT DOCUMENTS

| | | |
|---|---|---|
| 4,713,478 A | 12/1987 | Fayter, Jr. |
| 4,713,479 A | 12/1987 | Clark, Jr. et al. |

(Continued)

FOREIGN PATENT DOCUMENTS

CA 2232915 A1 9/1998

OTHER PUBLICATIONS

Viohl J., et al., "The Chemistry of Dental Filling Plastics," Construction of Plastics, pp. 21-27, 1986.
(Continued)

*Primary Examiner* — Tae H Yoon
(74) *Attorney, Agent, or Firm* — Ann M. Knab; Thad McMurray

(57) ABSTRACT

Dental material which contains at least one vinylcyclopropane of the general formulae I,

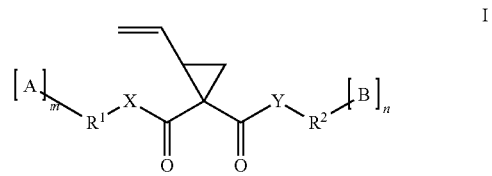

in which A, B independently of each other are in each case OH or COOH; X, Y independently of each other are in each case O or NH; $R^1$, $R^2$ independently of each other are in each case H or an aliphatic linear or branched $C_1$-$C_{10}$ hydrocarbon radical which can be interrupted by O, S or an ester group; and n, m independently of each other are in each case 0, 1 or 2, wherein, if X=Y=O, $R^1 \neq H$ and $R^2 \neq H$, n+m≥1. The vinylcyclopropanes are characterized by a low shrinkage and a high reactivity on radical polymerization and are suitable in particular for the preparation of dental materials.

20 Claims, 1 Drawing Sheet

(51) Int. Cl.
  C08L 33/00    (2006.01)
  A61K 6/00     (2006.01)
  C07C 69/743   (2006.01)
  C08F 22/10    (2006.01)
  C07C 233/58   (2006.01)
  C08F 220/10   (2006.01)
  C08F 222/14   (2006.01)
  C08F 222/36   (2006.01)

(52) U.S. Cl.
  CPC ......... *C07C 69/743* (2013.01); *C07C 233/58* (2013.01); *C08F 22/105* (2013.01); *C08F 220/10* (2013.01); *C08F 222/14* (2013.01); *C08F 222/36* (2013.01); C07C 2601/02 (2017.05)

(56) References Cited

U.S. PATENT DOCUMENTS

| | | | |
|---|---|---|---|
| 5,886,212 | A | 3/1999 | Rheinberger et al. |
| 7,365,222 | B2 | 4/2008 | Moszner et al. |
| 7,816,476 | B2 | 10/2010 | Moszner et al. |
| 2004/0062743 | A1* | 4/2004 | Huwig ............... A61K 8/36 424/78.26 |
| 2008/0319104 | A1* | 12/2008 | Klapdohr ............ A61K 6/0005 523/117 |
| 2012/0046668 | A1* | 2/2012 | Gantes ............... A61C 1/084 606/130 |
| 2012/0132104 | A1* | 5/2012 | Ruppert .............. A61K 6/0017 106/15.05 |

OTHER PUBLICATIONS

Gebhardt, A., "Generative Manufacturing Processes, Rapid Prototyping—Rapid Tooling—Rapid Manufacturing" Textbook, Edition 3, 2007.

Moszner et al., "Polymerization of Cyclic Monomers. VII. Synthesis and Radical Polymerization of 1,3-Bis [(1-alkoxycarbonyl-2-vinylcyclopropane-1-y) carboxy]benxenes," Journal of Applied Polymer Science, vol. 72, 1775-1782 (1999). John Wiley & Sons, Inc.

Moszner et al., "Synthesis and polymerization of vinylcyclopropanes," Macromol. Chem. Phys. 200, No. 10, 2173-2187 (1999). Wiley-VCH Verlag GmbH.

Moszner et al., "Polymerization of Cyclic Monomers, 10a,b, Synthesis and Radical Polymerization of Methyl 1-(Bicyclo[3,1,0]hex-1-yl]acrylate," Macromol. Rapod Commun., 24, 269-273 (2003). Wiley-VCH Verlag GmbH & Co. KGaA., Weinheim.

Moszner et al., "Synthesis and radical polymerization of bi- and trifunctional 2-vinylcyclopropanes," Macromol. Rapid. Commun., 18, 775-780 (1997). Hüthig & Wepf Verlag, Zug.

Moszner et al., "New Polymer-Chemical Developments in Clinical Dental Polymer Materials: Enamel-Dentin Adhesives and Restorative Composites," Journal of Polymer Science. 50, 4369-4402 (2012). Wiley Periodicals, Inc.

Nicholson et al., "The Chemistry of Modern Dental Filling Materials," J. Chem. Ed., vol. 76, No. 11, 1497-1501 (Nov. 1999).

Stansbury, J. W., "Curing Dental Resins and Composites by Photopolymerization," Journal of Esthetic Dentistry, 12, 300-308 (2000). University of Colorado Health Sciences Center, School of Dentistry, Aurora, Colorado.

Sanda et al., "Radical Copolymerization of 1,1-Bis(ethoxycarbonyl)-2-vinylcyclopropane and Methyl Methacrylate Accompanying Ring Opening and Cyclization," Macromolecules, 27, 3982-3985 (1994). American Chemical Society.

Sanda et al., "Synthesis and Radical Ring-Opening Polymerization of a Vinylcyclopropane Bearing a Cyclic Carbonate Moiety, 1-Vinyl-5,7-dioxaspiro[2.5]octan-6-one," Macromolecules, 27, 3986-3991 (1994). American Chemical Society.

Okazaki et al., "Synthesis and Radical Ring-Opening Polymerization Behavior of Bifunctional Vinylcyclopropane Bearing a Spiroacetal Moiety," Macromolecules, vol. 28, No. 18, 6026-6028 (1995).

Peutzfeldt, A., "Resin composites in dentistry: the monomer systems," European Journal of Oral Sciences, 105:97-116 (1997).

* cited by examiner

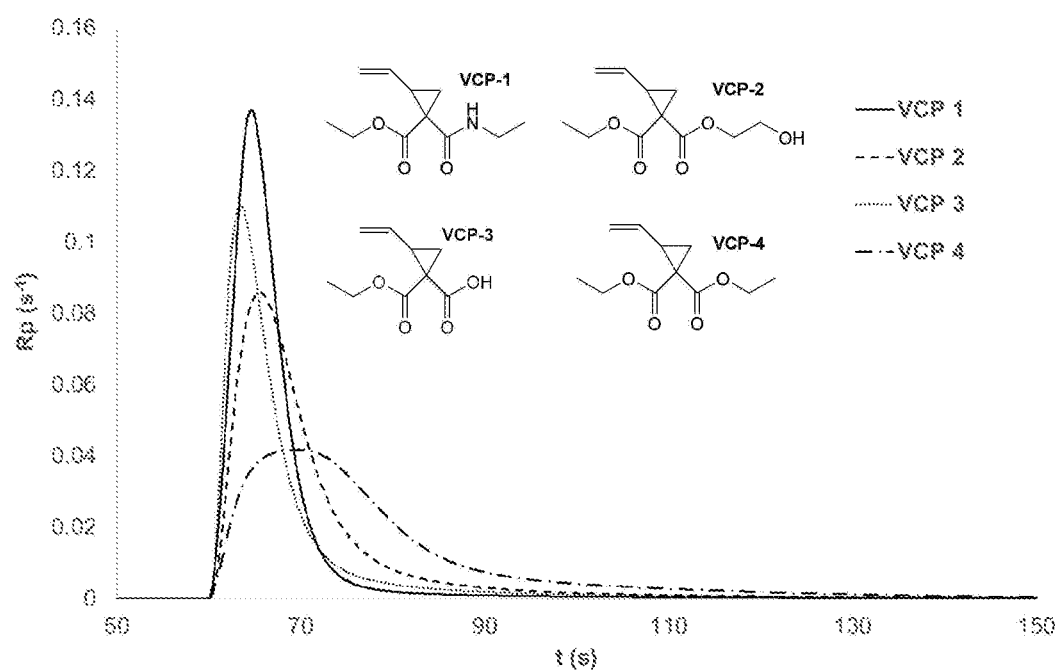

DENTAL MATERIALS BASED ON MONOFUNCTIONAL VINYLCYCLOPROPANE DERIVATIVES

CROSS-REFERENCE TO RELATED APPLICATIONS

This application claims priority to German patent application No. 102016214389.1 filed on Aug. 3, 2016, the disclosure of which is incorporated herein by reference in its entirety.

TECHNICAL FIELD

The present invention relates to dental materials based on monofunctional vinylcyclopropanes which have a high reactivity on radical polymerization. The materials are suitable in particular as cements, composites, coating materials, bondings and adhesives. In addition, they are suitable for the stereolithographic production of shaped bodies.

BACKGROUND OF THE INVENTION

The polymerizable organic matrix of dental resins, cements or composites primarily consists of a mixture of monomers, initiator components, stabilizers and pigments (J. Viohl, K. Dermann, D. Quast, S. Venz, Die Chemie zahnärztlicher Füllungskunststoffe [The chemistry of dental filling plastics], Carl Hanser Verlag, Munich-Vienna 1986, 21-27). Mixtures of dimethacrylates are usually used as resins (cf. A. Peutzfeldt, Resin composites in dentistry: the monomer systems, Eur. J. Oral. Sci. 105 (1997) 97-116; J. W. Nicolson, H. M. Anstice, The chemistry of modern dental filling materials, J. Chem Ed. 76 (1999) 1497-1501; J. W. Stansburry, Curing dental resins and composites by photopolymerization, J. Esthet. Dent., 12 (2000) 300-308; N. Moszner, T. Hirt, New Polymer-Chemical Developments in Clinical Dental Polymer Materials: Enamel-Dentin Adhesives and Restorative Composites, J. Polym. Sci. Part A: Polym. Chem. 50 (2012) 4369-4402).

A main disadvantage of the methacrylates used is that their polymerization is accompanied by a volume contraction, so-called polymerization shrinkage. In the case of dental materials, polymerization shrinkage can lead, among other things, to disadvantageous shrinkage stresses and to marginal gap formation in filling composites, to reduced substrate adhesion in fixing composites or coating materials and to impairment of the dimensional stability of prosthesis plastics. In this connection, radically polymerizable cyclic monomers have received much attention in the preparation of dental materials due to the considerably lower polymerization shrinkage compared with linear monomers, such as e.g. methacrylates (cf. R. K. Sadhir, R. M. Luck, Expanding Monomers, CRC Press, Boca Raton etc. 1992).

With respect to other known ring-opening monomers, such as methylene group-containing spiro orthocarbonates (SOCs), spiro orthoesters (SOEs) or bicyclic orthoesters (BOEs), vinylcyclopropanes are characterized by the fact that the vinylcyclopropyl (VCP) group is not sensitive to moisture and that polymers with high molar masses which contain only hydrolytically stable C—C bonds in the main chain are obtained in their radical polymerization. (N. Moszner, F. Zeuner, T. Völkel, V. Rheinberger, Macromol. Chem. Phys. 200 (1999) 2173).

From DE 198 12 888 A1 vinylcyclopropane derivatives and in particular vinylcyclopropane (meth)acrylates are known which can be copolymerized with acrylates and methacrylates.

Moreover, vinylcyclopropanes with several polymerizable groups are known. F. Sanda, T. Takata, T. Endo, Macromolecules 27 (1994) 3986 describe 1-vinyl-5,7-dioxaspiro[2.5]octan-6-one, a hybrid monomer which contains a vinylcyclopropane group and a cyclic carbonate group, and T. Okazaki, F. Sanda, T. Endo, Macromolecules 28 (1995) 6026 describe 1,10-bis(vinyl)-4,8,12,15-tetraoxatrispiro[2.2.2.2.2.2]pentadecane, a monomer in which two vinylcyclopropane groups are joined to each other via a hydrolysis-sensitive spiroacetal unit. Compared with monofunctional vinylcyclopropanes, these compounds do not have any improved radical copolymerizability with (meth)acrylic compounds.

EP 0 798 286 A1 relates to multifunctional vinylcyclopropane derivatives with two to six vinylcyclopropane groups which enable the preparation of crosslinked polymers.

Using the example of the radical copolymerization of 1,1-bis(ethoxycarbonyl)-2-vinylcyclopropane with methyl methacrylate (MMA), it could be shown (F. Sanda, T. Takata, T. Endo, Macromolecules, 27 (1994) 3982) that compared with methacrylates, vinylcyclopropanes are characterized by a lower radical polymerization capability, which considerably restricts their practical use. It is particularly disadvantageous that the known 1,1-bis(alkoxycarbonyl)-2-vinylcyclopropanes which are easy to obtain have a low photopolymerization activity.

EP 1 413 569 A1 discloses dental materials based on bicyclic cyclopropane derivatives, such as e.g. 2-[bicyclo[3.1.0]hex-1-yl]-acrylic acid methyl ester, which exhibit an improved reactivity on radical polymerization (N. Moszner, F. Zeuner, U.K. Fischer, V. Rheinberger, A. de Meijere, V. Bagutski, Macromol. Rapid. Commun. 24 (2003) 269). However, these more reactive monofunctional bicyclic cyclopropyl acrylates can only be obtained with great difficulty.

SUMMARY OF THE INVENTION

The object of the invention is to provide radically polymerizable dental materials which shrink only slightly on radical polymerization and which have a high radical polymerization reactivity, in particular on photopolymerization. The dental materials are to be suitable as adhesives, cements or filling composites as well as for the production of coatings and shaped bodies, for example for the stereolithographic production of shaped bodies. Moreover, the dental materials are to be based on monomers which are easy to obtain synthetically.

BRIEF DESCRIPTION OF THE DRAWINGS

Further advantages, details and features may be taken from the following description of an exemplary embodiment of the invention in conjunction with the drawing, in which:

FIG. 1 shows photopolymerization reactivity of various polymers of the invention.

DETAILED DESCRIPTION

This object is achieved by dental materials which contain at least one vinylcyclopropane with general formulae I:

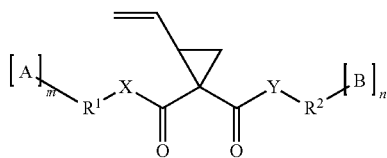

in which

A, B independently of each other are in each case OH or COOH,

X, Y independently of each other are in each case O or NH, $R^1$, $R^2$ independently of each other are in each case H or an aliphatic linear or branched $C_1$-$C_{10}$ hydrocarbon radical which can be interrupted by O, S or an ester group, an alicyclic or aromatic $C_6$-$C_{14}$ radical or an aromatic or non-aromatic heterocyclic radical which can contain 4 to 14 carbon atoms and 1 to 6 heteroatoms which are selected from N, O and/or S atoms, and n, m independently of each other are in each case 0, 1 or 2.

If X=Y=O, $R^1 \neq H$ and $R^2 \neq H$ then n+m≥1. The compounds of formula I are characterized by the fact that they have groups (CO—NH, OH, COOH) which are suitable for forming hydrogen bridge bonds.

Compounds of formula I in which A and B have the same meaning are preferred. Likewise, those compounds in which X and Y have the same meaning are preferred. $R^1$ and $R^2$ can be the same or preferably different.

Formula I and the remaining formulae shown herein cover all stereoisomeric forms as well as mixtures of different stereoisomeric forms, such as e.g. racemates. The formulae cover only those compounds that are compatible with the chemical valence theory. If, for example $R^1$=H, then m must=0, and if $R^2$=H, then n must=0. If m=0 and $R^1 \neq H$, the free valence at $R^1$ is saturated by H, and if n=0 and $R^2 \neq H$, the free valence at $R^2$ is accordingly saturated by H. The indication that a radical can be interrupted by a group or a heteroatom such as O is to be understood to mean that the group or the heteroatom is inserted into the carbon chain or the carbon ring of the radical, i.e. is bordered on both sides by carbon atoms. The number of heteroatoms is therefore smaller than the number of carbon atoms by at least 1 and the heteroatoms cannot be terminal. $C_1$ radicals cannot be interrupted. In the case of hydrocarbon radicals which contain carbon and heteroatoms, the number of heteroatoms is always less than the number of carbon atoms irrespective of substituents. The radicals $R^1$ and/or $R^2$ can be interrupted by one or more of the named atoms and groups. Preferred are radicals that are interrupted by one group or one atom, or particularly preferably are not interrupted.

The named cyclic radicals can be mono- or polycyclic groups. $R^1$ and/or $R^2$ can also be formed by a combination of the named radicals, for example by a combination of one or more aliphatic and one or more aromatic groups, e.g. an aliphatic-aromatic $C_7$-$C_{14}$ radical. Particularly preferred are radicals which contain a tricyclodecane group (TCD).

The compounds of formula I contain a radically polymerizable vinylcyclopropane group. Compounds with only one radically polymerizable group are referred to as monofunctional monomers here.

According to the invention, compounds of formula I are preferred in which the variables have the following meanings:

A OH,
m 0, 1 or 2,
$R^1$ H or a branched or preferably linear $C_1$-$C_6$ hydrocarbon radical which can be interrupted by O, wherein radicals which are not interrupted by O are preferred, wherein $R^1$ is preferably not H if X=O and m=0,
X O or NH, wherein X is preferably NH if m=0 and $R^1 \neq H$,
n 0,
$R^2$ a branched or preferably linear $C_1$-$C_3$ alkyl radical,
Y O;
or preferably
B OH,
n 0, 1 or 2,
$R^2$ H or a branched or preferably linear $C_1$-$C_6$ hydrocarbon radical which can be interrupted by O, wherein radicals which are not interrupted by O are preferred, wherein $R^2$ is preferably not H if Y=O and n=0,
Y O or NH, wherein Y is preferably NH if n=0 and $R^2 \neq H$,
m 0,
$R^1$ a branched or preferably linear $C_1$-$C_3$ alkyl radical
X O.

Particularly preferred are compounds of formula I in which the variables have the following meanings:

A OH,
m 0 or 1,
$R^1$ H or a linear $C_1$-$C_6$ hydrocarbon radical, wherein $R^1$ is preferably not H if X=O and m=0,
X O or NH, wherein X is NH if m=O and $R^1 \neq H$,
n 0,
$R^2$ a linear $C_1$-$C_3$ alkyl radical
Y O;
or preferably
B OH,
n 0 or 1,
$R^2$ H or a linear $C_1$-$C_6$ hydrocarbon radical, wherein $R^2$ is preferably not H if Y=O and n=0,
Y O or NH, wherein Y is NH if n=O and $R^2 \neq H$,
m 0,
$R^1$ a linear $C_1$-$C_3$ alkyl radical,
X O.

The vinylcyclopropanes of formula I and thus also the dental materials based on them are characterized by a low shrinkage and a high reactivity on radical polymerization.

In addition, the vinylcyclopropanes of formula I have a low viscosity and are therefore particularly suitable as diluting monomers for viscous monomers. The monomers of formula I preferably have a viscosity of from 10 to 2000 mPa·s, measured at 23° C. with a rotational viscometer. In addition, monomers with low viscosity permit the preparation of highly fluid dental materials, which can be advantageous e.g. for the preparation of adhesives or for the preparation of materials for the stereolithographic production of shaped bodies. In the case of materials containing filler, such as e.g. filling composites, they make it possible to use higher quantities of filler.

A subject of the present invention is also the use of vinylcyclopropanes of formula I for the preparation of dental materials, in particular dental cements, composites, coating materials, bondings and adhesives, as well as for the preparation of materials for the stereolithographic production of shaped bodies. A further subject of the invention are shaped bodies, polymers and copolymers which can be obtained by homo- or copolymerization of the vinylcyclopropanes of formula I.

Vinylcyclopropanes of general formula I can be easily prepared. The synthesis of 1,1-di(alkoxycarbonyl)-substituted 2-vinylcyclopropanes can take place according to known methods (cf. U.S. Pat. Nos. 4,713,478 and 4,713,479) by reacting trans-1,4-dihalogen-but-2-enes with corresponding malonic acid esters:

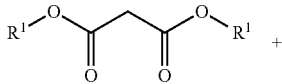

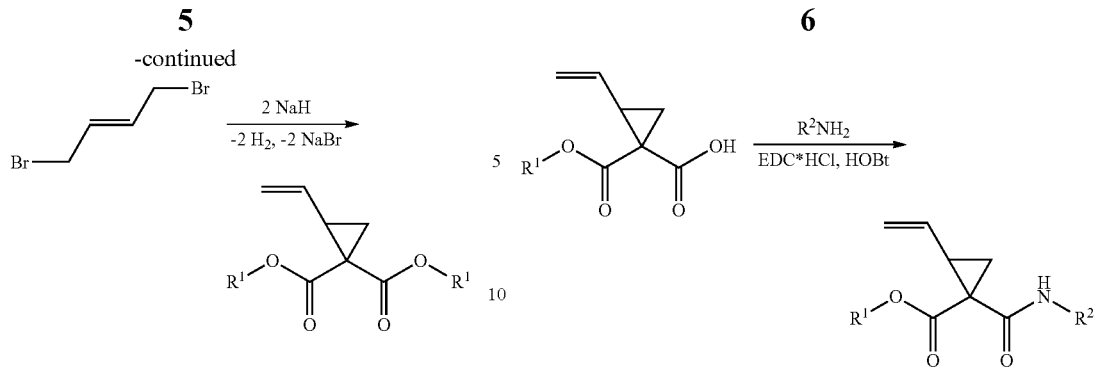

For example:

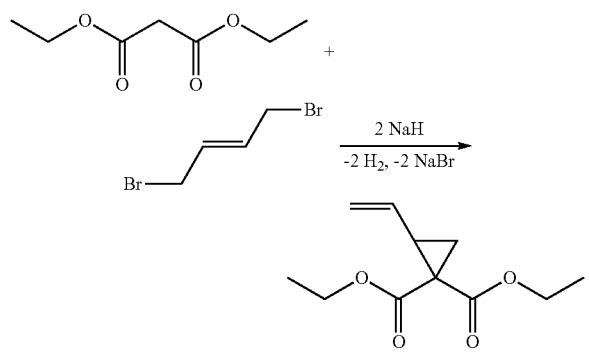

From the 1,1-di(alkoxycarbonyl)-substituted 2-vinylcyclopropanes, 2-vinylcyclopropane-1-alkoxycarbonyl-1-carboxylic acids according to the invention can be prepared by partial alkaline hydrolysis:

For example:

From the 2-vinylcyclopropane-1-alkoxycarbonyl-1-carboxylic acids according to the invention, corresponding amides according to the invention can be synthesized by reaction with primary amines in the presence of N-(3-dimethylaminopropyl)-N'-ethylcarbodiimide (EDC*HCl) and 1-hydroxybenzotriazol (HOBt):

For example:

In addition, from the 2-vinylcyclopropane-1-alkoxycarbonyl-1-carboxylic acids according to the invention, the hydroxyalkyl derivatives according to the invention can be obtained by reaction with diols in the presence of dicyclohexylcarbodiimide (DCC) and 4-dimethylaminopyridine (DMAP):

For example:

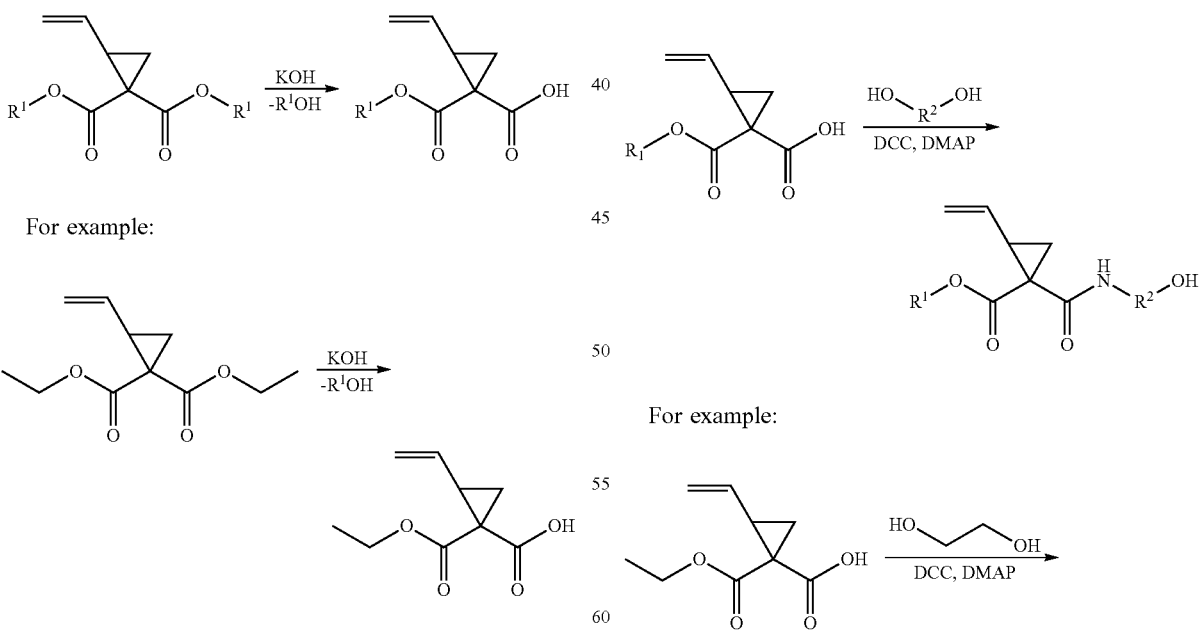

Furthermore, from 1,1-di(alkoxycarbonyl)-substituted 2-vinylcyclopropanes, 2-vinylcyclopropane-1,1-dicarboxylic acid can be prepared by complete alkaline hydrolysis:

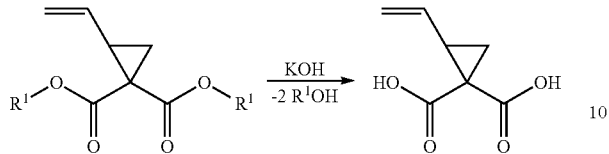

From the 2-vinylcyclopropane-1,1-dicarboxylic acid, the corresponding amides according to the invention can be prepared by reaction with primary amines in the presence of N-(3-dimethylaminopropyl)-N'-ethylcarbodiimide (EDC*HCl) and 1-hydroxybenzotriazole (HOBt):

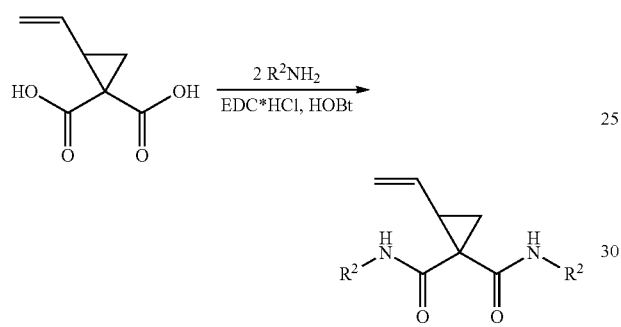

For example:

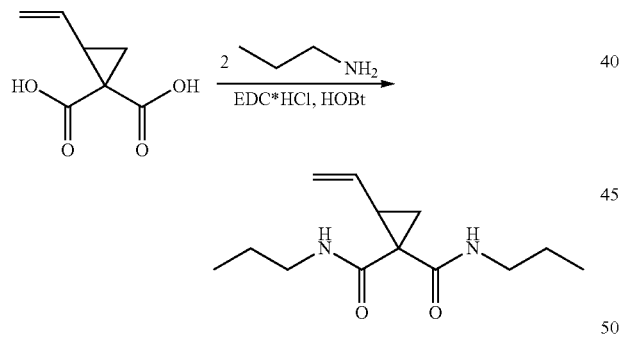

Preferred examples of the vinylcyclopropanes according to the invention of general formulae I are:

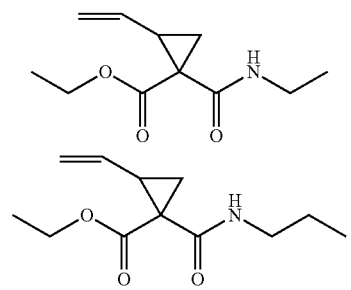

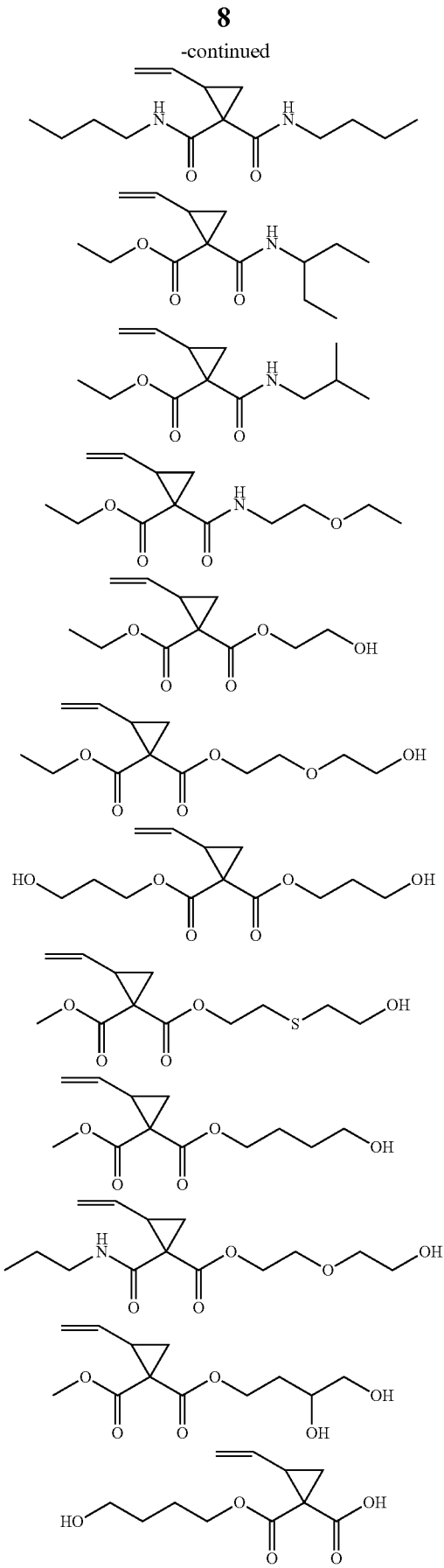

-continued

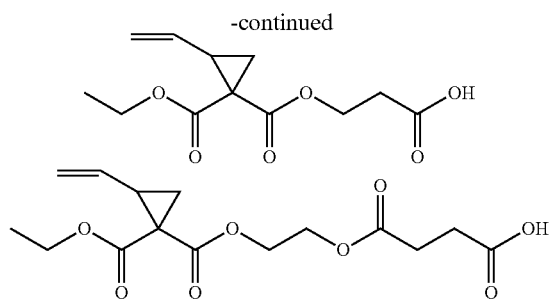

The polymerizable urethane group-containing vinylcyclopropanes of general formula I are mostly liquid and surprisingly exhibit a considerably improved radical polymerizability, in particular on photopolymerization, compared with 1,1-bis(alkoxycarbonyl)-2-vinylcyclopropanes and a lower polymerization shrinkage compared with non-cyclic methacrylates. Dental materials such as fixing cements or filling composites can thus be prepared likewise with reduced polymerization shrinkage.

The (dental) materials according to the invention preferably contain 2 to 95 wt.-%, particularly preferably 2 to 85 wt.-%, more preferably 5 to 70 wt.-% and most preferably 10 to 50 wt.-% vinylcyclopropane(s) of general formula I, in each case relative to the total mass of the material.

In addition to one or more vinylcyclopropanes of general formula I, the materials preferably contain at least one further radically polymerizable monomer. Other vinylcyclopropanes such as 1,1-di(ethoxycarbonyl)- or 1,1-di (methoxycarbonyl)-2-vinylcyclopropane, bis(2-vinylcyclopropane-1-carboxylic acid ethyl ester-1-carbonamido)-2,2-dimethyl-4-methylhexane, 1,8-bis(2-vinylcyclopropane-1-carboxylic acid ethyl ester-1-carbonyloxy)-3,6-dioxaoctane or the esters of 1-ethoxycarbonyl- or 1-methoxycarbonyl-2-vinylcyclopropane carboxylic acid with ethylene glycol, 1,1,1-trimethylolpropane, 1,4-cyclohexanediol or resorcinol are preferred as further radically polymerizable monomers, such as bis-(2-vinyl-1,1-dicarboxylic acid monoethyl ester) resorcinyl ester, and in particular the 2-vinylcyclopropanes described in N. Moszner, F. Zeuner, V. Rheinberger, Macromol. Rapid Commun. 18 (1997) 775-780, and N. Moszner, F. Zeuner, T. Völkel, U. K. Fischer, V. Rheinberger, J. Appl. Polym. Sci. 72 (1999) 1775-1782. Further preferred are the bicyclic cyclopropane derivatives disclosed in EP 1 413 569 A1, in particular 2-(bicyclo[3.1.0]hex-1-yl)acrylic acid methyl or ethyl ester or disubstitution products thereof in the 3 position, such as (3,3-bis(ethoxycarbonyl)bicyclo[3.1.0] hex-1-yl)acrylic acid methyl or ethyl ester.

Likewise preferred are the cyclopropyl acrylates disclosed in EP 1 688 125 A1, in particular {3,3-bis(ethoxycarbonyl)bicyclo[3.1.0]hexa-1-yl}acrylic acid methyl ester and 2-{3-acetyl-3-ethoxycarbonyl-bicyclo[3.1.0]hexa-1-yl}acrylic acid methyl ester.

In addition, the dental materials can also contain radically polymerizable mono- or polyfunctional (meth)acrylic acid derivatives. By monofunctional monomers is meant herein in all cases compounds with one, by multifunctional monomers compounds with two or more, preferably 2 to 4, radically polymerizable groups.

Preferred mono- or multifunctional methacrylates are methyl, ethyl, 2-hydroxyethyl, butyl, benzyl, tetrahydrofurfuryl or isobornyl (meth)acrylate, p-cumylphenoxyethylene glycol methacrylate (CMP-1E), bisphenol A di(meth)acrylate, bis-GMA (an addition product of methacrylic acid and bisphenol A diglycidyl ether), ethoxylated or propoxylated bisphenol A dimethacrylate, such as e.g. the bisphenol A dimethacrylate 2-[4-(3-methacryloyloxyethoxyethyl)phenyl]-2-[4-(3-methacryloyloxyethyl)phenyl]-propane) (SR-348c) with 3 ethoxy groups or 2,2-bis[4-(2-(meth)acryloxypropoxy)phenyl]propane, UDMA (an addition product of 2-hydroxyethyl methacrylate (HEMA) and 2,2,4-trimethylhexamethylene diisocyanate), TMX-UDMA (an addition product of a mixture of HEMA and hydroxypropyl methacrylate (HPMA) with α,α,α',α'-tetramethyl-m-xylylene diisocyanate (TMXDI)), di-, tri- or tetraethylene glycol di(meth)acrylate, trimethylolpropane tri(meth)acrylate, pentaerythritol tetra(meth)acrylate, as well as glycerol di- and trimethacrylate, 1,4-butanediol di(meth)acrylate, 1,10-decanediol di(meth)acrylate ($D_3MA$) or 1,12-dodecanediol di(meth)acrylate.

Moreover, the dental materials can advantageously also contain radically polymerizable, acid group-containing monomers, such as e.g. polymerizable carboxylic acids, phosphonic acids and phosphoric acid esters. Preferred examples of polymerizable carboxylic acid monomers are maleic acid, 2-(hydroxymethyl)acrylic acid and 4-(meth) acryloyloxyethyltrimellitic acid anhydride. Preferred examples of suitable phosphonic acid monomers are 2-methacryloyloxyethyl phosphonic acid, 2-methacrylamidoethyl phosphonic acid, 2-[4-(dihydroxyphosphoryl)-2-oxa-butyl]-acrylic acid ethyl or -2,4,6-trimethylphenyl ester. Preferred examples of suitable acidic polymerizable phosphoric acid esters are 2-methacryloyloxypropyl dihydrogen phosphate, 2-methacryloyloxyethyl dihydrogen phosphate, 2-methacryloyloxyethylphenyl hydrogen phosphate, dipentaerythritol pentamethacryloyloxy phosphate, 10-methacryloyloxydecyl dihydrogen phosphate and 6-(methacrylamido)hexyl dihydrogen phosphate. Acidic monomers primarily serve to improve the adhesion of the materials to dentine and/or tooth enamel. The amount of acidic monomers preferably lies in the range of from 0 to 20 wt.-%, preferably 0 to 15 wt.-% and particularly preferably 0 to 10 wt.-%, relative to the total mass of the dental material.

According to the invention, materials are preferred which contain at least one multifunctional radically polymerizable monomer, i.e. materials which contain a monomer with two or more, preferably 2 to 4, radically polymerizable groups.

According to the invention, those dental materials which contain at least one monofunctional vinylcyclopropane with general formulae II as comonomer are preferred:

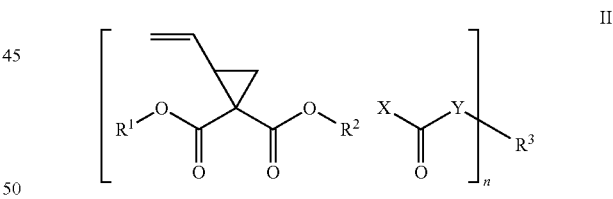

in which
X, Y in each case are O or NH, wherein X and Y cannot have the same meaning,
$R^1$ is a linear or branched $C_1$-$C_8$ alkyl radical which can be interrupted by O, S, an ester group and/or a urethane group,
$R^2$ is a linear or branched $C_2$-$C_{10}$ alkylene radical which can be interrupted by O, S, an ester group and/or a urethane group,
$R^3$ is a hydrocarbon radical with 1 to 20 carbon atoms which additionally can contain one or more N, O or S atoms, and
n is 1, 2, 3 or 4, preferably 1 or 2.

The urethane group optionally present in $R^1/R^2$ is preferably a non-N-substituted group of the formula —NH—CO—O—. The radicals $R^1$ and/or $R^2$ of formula II can be interrupted by one or more of the named atoms and groups.

Preferred are radicals that are interrupted by one group or one atom, or particularly preferably are not interrupted.

The radical $R^3$ of formula II is substituted n times by the expression in brackets. $R^3$ is a hydrocarbon radical with 1 to 20 carbon atoms which can contain one or more N, O or S atoms. $R^3$ is preferably an aliphatic linear or branched $C_1$-$C_{20}$ hydrocarbon radical which can be interrupted by O, S or an ester group, an alicyclic or aromatic $C_6$-$C_{14}$ radical or an aromatic or non-aromatic heterocyclic radical which can contain 4 to 20 carbon atoms and 1 to 6 heteroatoms which are selected from N, O and/or S atoms. The named cyclic radicals can be mono- or polycyclic groups. $R^3$ can also be formed by a combination of the named radicals, for example by a combination of one or more aliphatic and one or more aromatic groups, e.g. an aliphatic-aromatic $C_7$-$C_{20}$ radical. Particularly preferred are radicals which contain a tricyclodecane group (TCD).

According to the invention, those compounds of formula II are preferred in which the variables have the following meanings:

X, Y in each case O or NH, wherein X and Y cannot have the same meaning,
$R^1$ a branched or preferably linear $C_1$-$C_4$ alkyl radical,
$R^2$ a branched or preferably linear $C_2$-$C_4$ alkyl radical,
$R^3$ an aliphatic linear or branched $C_1$-$C_{20}$ hydrocarbon radical, an aromatic $C_6$-$C_{14}$ radical, an aromatic or non-aromatic heterocyclic radical which contains 4 to 12 carbon atoms and 1 to 2 heteroatoms, which are selected from N or O atoms, an alicyclic $C_6$-$C_{12}$ hydrocarbon radical, wherein in all cases the cyclic radicals can be mono- or polycyclic groups, or an aliphatic-aromatic $C_7$-$C_{20}$ radical,
n 1 or 2.

According to the invention, compounds of formula II are particularly preferred in which the variables have the following meanings:

X, Y in each case 0 or NH, wherein X and Y cannot have the same meaning,
$R^1$ a methyl or ethyl radical,
$R^2$ a linear $C_2$-$C_4$ alkylene radical,
$R^3$ an aliphatic linear or branched $C_1$-$C_{10}$ hydrocarbon radical, an aromatic $C_6$-$C_{14}$ radical, an alicyclic $C_6$-$C_{12}$ hydrocarbon radical, wherein in all cases the cyclic radicals can be mono- or polycyclic groups, or an aliphatic-aromatic $C_7$-$C_{15}$ radical,
n 1 or 2.

The dental materials according to the invention preferably furthermore contain an initiator for the radical polymerization. Benzophenone, benzoin and derivatives thereof or α-diketones or derivatives thereof, such as 9,10-phenanthrenequinone, 1-phenyl-propane-1,2-dione, diacetyl or 4,4'-dichlorobenzyl are preferred for the initiation of the radical photopolymerization. Camphorquinone and 2,2-dimethoxy-2-phenyl-acetophenone are particularly preferably used, and quite particularly preferably α-diketones combined with amines as reductants, such as e.g. 4-(dimethylamino)-benzoic acid ethyl ester, N,N-dimethylaminoethyl methacrylate, N,N-dimethyl-sym.-xylidine or triethanolamine. Norrish type I photoinitiators, above all acyl- or bisacylphosphine oxides, such as for example the commercially available compounds 2,4,6-trimethylbenzoyl diphenylphosphine oxide and bis(2,4,6-trimethylbenzoyl)phenylphosphine oxide are also particularly suitable. Monoacyl trialkyl or diacyl dialkyl germanium, triacyl alkyl and tetraacyl germanium compounds, such as e.g. benzoyltrimethylgermanium, dibenzoyldiethylgermanium or bis(4-methoxybenzoyl)diethylgermanium as well as tetrabenzoylgermanium are also particularly suitable. Mixtures of the different photoinitiators can also be used, such as e.g. dibenzoyldiethylgermanium in combination with camphorquinone and 4-dimethylaminobenzoic acid ethyl ester or tetrabenzoylgermanium. Advantageously, initiator combinations can also be used which additionally contain aromatic diaryliodonium or triarylsulfonium salts, for example the commercially available compounds 4-octyloxyphenyl-phenyl-iodonium hexafluoroantimonate or isopropylphenyl-methylphenyl-iodonium tetrakis(pentafluorophenyl)borate.

Preferably, redox-initiator combinations, such as e.g. combinations of benzoyl peroxide with N,N-dimethyl-sym.-xylidine or N,N-dimethyl-p-toluidine, are used as initiators for a polymerization carried out at room temperature. In addition, redox systems consisting of peroxides or hydroperoxides and reducing agents, such as e.g. ascorbic acid, barbiturates, thioureas or sulfinic acids, are also particularly suitable. Moreover, compounds of transition metals which exhibit at least two stable valency stages can be used as redox catalysts. They are, above all, compounds of the elements copper, iron, vanadium, nickel or cobalt, wherein copper compounds are particularly preferred and these are preferably used as highly organosoluble compounds, such as e.g. acetylacetonate, naphthenate or 2-ethylhexanoate.

Dental materials which contain at least one photoinitiator are preferred according to the invention. The materials can additionally contain further initiators.

In addition, the compositions used according to the invention preferably also contain at least one organic or particularly preferably inorganic particulate filler, for example to improve the mechanical properties or to adjust the viscosity. Preferred inorganic particulate fillers are amorphous spherical materials based on oxides, such as $SiO_2$, $ZrO_2$ and $TiO_2$ or mixed oxides of $SiO_2$, $ZrO_2$ and/or $TiO_2$, nanoparticulate or microfine fillers, such as pyrogenic silica or precipitated silica (weight-average particle size of 10-1000 nm), as well as minifillers, such as quartz, glass ceramic or glass powder with a weight-average particle size of from 0.01 to 1 μm. Further preferred fillers are X-ray opaque fillers, such as ytterbium trifluoride, nanoparticulate tantalum(V) oxide, barium sulfate, mixed oxides of $SiO_2$ with ytterbium(III) oxide or tantalum(V) oxide (weight-average particle size of 10-1000 nm) and X-ray opaque glass powder, e.g. barium or strontium aluminium silicate glasses (weight-average particle size of 0.2-10 μm).

To improve the bond between the filler particles and the crosslinked polymerization matrix, the filler particles can be surface-modified with suitable coupling reagents. For $SiO_2$-based fillers such as $SiO_2$, quartz, glass ceramic or glass powder, trialkoxysilanes, such as e.g. 3-methacryloyloxypropyltrimethoxysilane, are particularly suitable. Trialkoxysilanes which contain vinylcyclopropane groups are preferred, quite particularly the vinylcyclopropanesilanes described in EP 0 867 444 A2, wherein in particular the 1-methoxy- or 1-ethoxycarbonyl-1-[(3-trimethoxy- or 3-triethoxysilyl)propylaminocarbonyl)]-2-vinylcyclopropanes are preferred. Specifically, vinylcyclopropanesilanes with the following structures are particularly suitable:

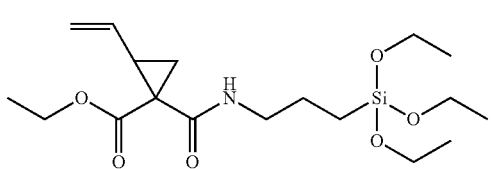

-continued

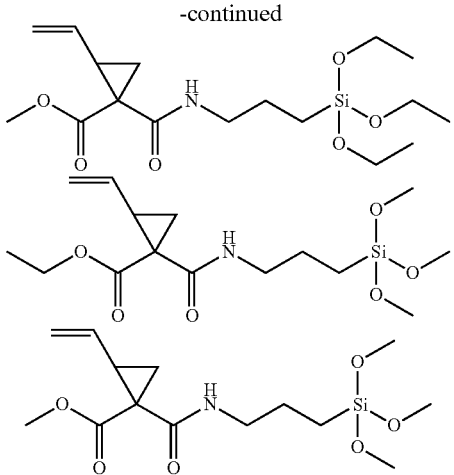

For the surface-modification of non-silicate fillers, e.g. of $ZrO_2$ or $TiO_2$, functionalized acidic phosphates, such as e.g. 10-methacryloyloxy dihydrogen phosphate can also be used.

Optionally, the compositions used according to the invention can contain one or more further additives, above all solvents, preferably water, ethanol or a mixture thereof, and stabilizers, such as e.g. polymerization stabilizers, flavourings, dyes, microbiocidal active ingredients, fluoride-ion-releasing additives, optical brighteners, plasticizers and/or UV absorbers.

According to the invention, those dental materials are preferred which contain the following components:
a) 2 to 95 wt.-%, preferably 2 to 90 wt.-% and particularly preferably 10 to 85 wt.-% of at least one vinylcyclopropane of general formula I,
b) 0.01 to 5 wt.-%, preferably 0.1 to 3.0 wt.-%, particularly preferably 0.2 to 2 wt.-% of at least one initiator for the radical polymerization, preferably a photoinitiator,
c) 0 to 80 wt.-%, preferably 0 to 60 wt.-% and particularly preferably 0 to 50 wt.-% of other monomer(s) and optionally
d) 0 to 85 wt.-%, preferably 0 to 80 wt.-% filler(s).

The filler content is determined decisively by the desired application of the dental material. Dental materials for use as coating material particularly preferably contain 0 to 40 wt.-%, dental materials for use as cement preferably contain 10-70 wt.-% and dental materials for use as filling material (filling composite) preferably contain 10-85 wt.-% filler(s).

Dental materials for use as filling material particularly preferably have the following composition:
a) 2 to 50 wt.-%, preferably 5 to 50 wt.-% and particularly preferably 10 to 50 wt.-% of at least one vinylcyclopropane of general formula I,
b) 0.1 to 3 wt.-%, preferably 0.2 to 3.0 wt.-%, particularly preferably 0.2 to 1 wt.-% of at least one initiator for the radical polymerization, preferably a photoinitiator,
c) 0 to 50 wt.-%, preferably 0 to 40 wt.-% and particularly preferably 0 to 30 wt.-% of other monomer(s), and
d) 40 to 85 wt.-%, preferably 40 to 80 wt.-% filler(s).

Unless otherwise indicated, all quantities herein relate to the total mass of the material. The individual quantity ranges can be chosen separately.

Those materials which consist of the named components are particularly preferred. Furthermore, those materials in which the individual components are in each case selected from the above-named preferred and particularly preferred substances are preferred.

According to the invention, those dental materials which exclusively contain monomers which have vinylcyclopropyl (VCP) groups as radically polymerizable groups are particularly preferred.

The materials according to the invention are particularly suitable as dental materials, in particular as dental adhesives, cements, filling composites and veneering materials, and as materials for the production of prostheses, artificial teeth, inlays, onlays, crowns and bridges. Compared with materials based on dimethacrylates they are characterized by considerably lower polymerization shrinkage, and compared with known polymerizable cyclopropane derivatives by a better polymerization reactivity, in particular on photopolymerization.

The dental materials are suitable primarily for intraoral application by the dentist for the restoration of damaged teeth (clinical materials), e.g. as dental cements, filling composites and veneering materials. However, they can also be used extraorally, for example in the production or repair of dental restorations, such as prostheses, artificial teeth, inlays, onlays, crowns and bridges (technical materials). The materials are suitable in particular for the production of shaped bodies, for example of dental restorations, by generative processes, in particular by stereolithography or 3D printing (cf. A. Gebhardt, Generative Fertigungsverfahren [Generative manufacturing processes], 3rd ed., Carl Hanser Verlag, Munich 2007).

The invention is explained in more detail in the following with reference to examples.

EXAMPLES

Example 1

Synthesis of 1-ethoxycarbonyl-1-ethylcarbamoyl-2-vinylcyclopropane (VCP 1)

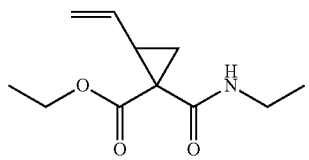

To a stirred solution of 1-ethoxycarbonyl-2-vinylcyclopropane carboxylic acid (VCP 3, 2.76 g, 15.0 mmol), which was prepared by partial hydrolysis of 1,1-bis(ethoxycarbonyl)-2-vinylcyclopropane (VCP 4) (cf. N. Moszner, F. Zeuner, V. Rheinberger, Macromol. Rapid. Commun. 18 (1997) 775-780) in anhydrous methylene chloride (20.0 ml), 1-hydroxybenzotriazol (HOBt, 2.03 g, 15.0 mmol) was added under argon. The solution was cooled to 0° C. and then ethylamine was added (2.0 M in THF, 7.5 ml, 15.0 mmol). A solution of N-(3-dimethylaminopropyl)-N'-ethylcarbodiimide (EDC*HCl, 3.45 g, 18.0 mmol) in anhydrous methylene chloride (40.0 ml) was added dropwise to the reaction mixture. It was stirred at 0° C. for 1 h and at RT for 15 h. The mixture was washed with a saturated sodium hydrogen carbonate solution (2×50 ml). The organic phase was dried over anhydrous sodium sulfate. The solvent was distilled off in a vacuum and the crude product was purified by chromatography (flash silica gel with ethyl acetate/hexane: 2/8). 2.63 g (83% yield) of a colourless liquid was obtained as a mixture of diastereoisomers (ratio: approx. 9/1).

NMR analysis of the main isomer: $^1$H NMR (400 MHz, CDCl$_3$): δ=1.17 (t, $^3J_{HH}$=7.4 Hz, 3H, NHCH$_2$CH$_3$); 1.29 (t, $^3J_{HH}$=7.1 Hz, 3H, OCH$_2$CH$_3$); 1.85 (dd, $^2J_{HH}$=4.2 Hz, $^3J_{HH}$=7.9 Hz, 1H, CH$_2$CHCH=CH$_2$); 2.05 (dd, $^2J_{HH}$=4.2 Hz, $^3J_{HH}$=9.1 Hz, 1H, CH$_2$CHCH=CH$_2$); 2.53 (q, $^3J_{HH}$=8.6 Hz, 1H, CH$_2$CHCH=CH$_2$); 3.24-3.41 (m, 2H, CH$_2$NH); 4.11-4.26 (m, 2H, CH$_2$O); 5.12-5.19 (m, 1H, CH$_2$=CH); 5.29-5.37 (m, 1H, CH$_2$=CH); 5.59-5.71 (m, 1H, CH$_2$=CH); 8.34 (s, NH). $^{13}$C NMR (101 MHz, CDCl$_3$): δ=14.2 (CH$_3$); 14.7 (CH$_3$); 21.2 (CH$_2$CHCH=CH$_2$); 34.2 (COCO); 34.8 (CH$_2$NH); 36.7 (CH$_2$CHCH=CH$_2$); 61.4 (CH$_2$O); 119.4 (CH$_2$=CH); 133.4 (CH$_2$=CH); 167.7 (OC=O); 171.4 (NHC=O).

Example 2

Synthesis of 1-(2-hydroxyethoxycarbonyl)-1-ethoxycarbonyl-2-vinylcyclopropane (VCP 2)

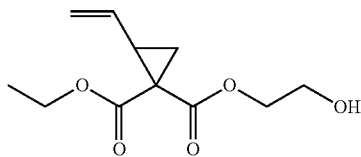 [SMILES: C=CC1CC1(C(=O)OCC)C(=O)OCCO]

To a stirred solution of 1-ethoxycarbonyl-2-vinylcyclopropane carboxylic acid (VCP 3, 36.8 g, 200 mmol), ethylene glycol (49.7 g, 800 mmol) and 4-dimethylaminopyridine (DMAP, 1.22 g, 1.0 mmol) in anhydrous methylene chloride (30.0 ml), dicyclohexylcarbodiimide (DCC, 41.2 g, 200 mmol) was added in portions under argon. It was stirred at 0° C. for 30 min and at RT for 15 h. The reaction mixture was suctioned over a frit and the residue was washed with methylene chloride (3×40 ml). The organic phase was washed with water (150 ml) and the aqueous phase extracted with dichloromethane (DCM) (2×30 ml). The combined organic phases were dried over anhydrous sodium sulfate. The solvent was distilled off in a vacuum and the crude product was purified by chromatography (flash silica gel with ethyl acetate/hexane: 1/3). 32.44 g (71% yield) of a colourless liquid was obtained as a mixture of diastereoisomers (ratio: approx. 9/1).

NMR analysis of the main isomer: $^1$H NMR (400 MHz, CDCl$_3$): δ=1.27 (t, $^3J_{HH}$=7.1 Hz, 3H, OCH$_2$CH$_3$); 1.60 (dd, $^2J_{HH}$=5.0 Hz, $^3J_{HH}$=9.0 Hz, 1H, CH$_2$CHCH=CH$_2$); 1.77 (dd, $^2J_{HH}$=5.0 Hz, $^3J_{HH}$=7.7 Hz, 1H, CH$_2$CHCH=CH$_2$); 2.62 (q, $^3J_{HH}$=8.5 Hz, 1H, CH$_2$CHCH=CH$_2$); 3.82 (t, $^3J_{HH}$=4.6 Hz, CH$_2$OH); 4.14-4.29 (m, $^3$H, CH$_2$OCO); 4.38 (dt, $^2J_{HH}$=10.7 Hz, $^3J_{HH}$=4.8 Hz, 1H, CH$_2$OCO); 5.13-5.20 (m, 1H, CH$_2$=CH); 5.27-5.37 (m, 1H, CH$_2$=CH); 5.41-5.53 (m, 1H, CH$_2$=CH). $^{13}$C NMR (101 MHz, CDCl$_3$): δ=14.2 (CH$_3$); 20.8 (CH$_2$CHCH=CH$_2$); 31.8 (CH$_2$CHCH=CH$_2$); 35.7 (COCO); 60.9 (CH$_2$OH); 61.6 (CH$_2$OCO); 67.1 (CH$_2$OCO); 119.0 (CH$_2$=CH); 132.7 (CH$_2$=CH); 167.4 (C=O); 169.9 (C=O).

Example 3

Determination of the Reactivity in the Photopolymerization

The reactivity of 1-ethoxycarbonyl-1-ethylcarbamoyl-2-vinylcyclopropane (VCP 1), 1-(2-hydroxyethoxycarbonyl)-1-ethoxycarbonyl-2-vinylcyclopropane (VCP 2), 1-ethoxycarbonyl-2-vinylcyclopropane carboxylic acid (VCP 3) and 1,1-bis(ethoxycarbonyl)-2-vinylcyclopropane (VCP 4) was investigated. In each case 0.5 mol % bis(4-methoxybenzoyl)diethylgermanium (Ivocerin®, Ivoclar Vivadent AG) was added to each monomer. Each mixture was polymerized in a Diamond Differential Scanning calorimeter (Perkin Elmer) with photopolymerization attachment by irradiation with an LED lamp (Bluephase, Ivoclar Vivadent AG) for 2 min at 37° C. The results are reproduced in FIG. 1. The vinylcyclopropanes according to the invention VCP 1, VCP 2 and VCP 3 exhibit a considerably higher maximum of the polymerization rate compared with reference compound VCP 4. The results thus prove a considerably higher photopolymerization reactivity of VCP 1 to 3 according to the invention compared with reference compound VCP 4.

Example 4

Preparation of Composites

Using a kneader, paste-like composites with the compositions stated in Table 1, based on monomers VCP 5/VCP 1 (8/2: wt./wt.), VCP 5/VCP 3 (8/2: wt./wt.) and UDMA/AAEMA (8/2: wt./wt.), were prepared. 1,6-Bis(2-vinylcyclopropane-1-carboxylic acid ethyl ester-1-carbonamido)-2,2-dimethyl-4-methylhexane (VCP 5) was synthesized from VCP 3 and 2,2,4-trimethylhexamethylenediamine (cf. P. P. Contreras, C. Kuttner, A. Fery, U. Stahlschmidt, V. Jerome, R. Freitag, S. Agarwal, Chem. Commun. 51 (2015) 11899-11902).

VCP-5

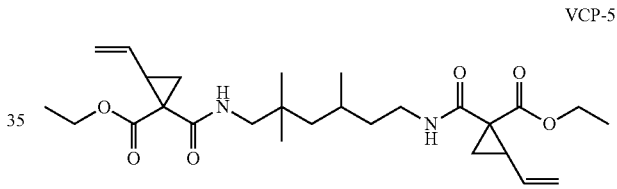

Corresponding test pieces were prepared from the materials, irradiated twice for 3 mins with a dental light source (Spectramat®, Ivoclar Vivadent AG) and thus cured. The flexural strength and the flexural modulus of elasticity were determined according to ISO standard 4049 (Dentistry—Polymer-based filling, restorative and luting materials) (Table 2). The measurements were carried out after 24 h storage in water (37° C.). The shrinkage was determined according to the buoyancy method (Table 2). Composites A and B based on the vinylcyclopropanes according to the invention VCP 1 and VCP 3 have a considerably lower polymerization shrinkage than the methacrylate-based composite C with comparable mechanical properties.

TABLE 1

| Composition of the prepared composites | | | |
|---|---|---|---|
| Component | Composite A (wt.-%) | Composite B (wt.-%) | Composite C*) (wt.-%) |
| VCP 1 | 4.0 | — | — |
| VCP 3 | — | 4.0 | — |
| VCP 5 | 15.8 | 15.8 | — |
| AAEMA[2)] | — | — | 4.0 |
| UDMA[1)] | — | — | 15.8 |
| Ivocerin®[7)] (Initiator) | 0.2 | 0.2 | 0.2 |
| Barium-aluminium-borosilicate glass filler[3)] | 51.7 | 51.7 | 51.7 |
| SiO$_2$—ZrO$_2$ Spherosil[4)] | 10.1 | 10.1 | 10.1 |

TABLE 1-continued

Composition of the prepared composites

| Component | Composite A (wt.-%) | Composite B (wt.-%) | Composite C*) (wt.-%) |
|---|---|---|---|
| Ytterbium fluoride YbF$_3$[5] | 17.2 | 17.2 | 17.2 |
| Aerosil OX-50[6] | 1.0 | 1.0 | 1.0 |

*)Comparison example
[1] Urethane dimethacrylate from 2 mol 2-hydroxyethyl methacrylate and 1 mol 2,2,4-trimethylhexamethylene diisocyanate-1,6
[2] 2-(Methacryloyloxy)ethyl acetoacetate
[3] Glass powder GM 27884, 1 μm, silanized (Schott)
[4] Tokoyama Soda
[5] Auer Remy
[6] Evonik
[7] Bis(4-methoxybenzoyl)diethylgermanium (Ivoclar Vivadent AG)

TABLE 2

Mechanical properties and volume shrinkage

| Composite | Flexural strength (MPa) | Flexural modulus of elasticity (GPa) | Volume shrinkage (Vol.-%) |
|---|---|---|---|
| A | 135.0 ± 6.3 | 10.1 ± 0.3 | 2.4 ± 0.2 |
| B | 136.4 ± 5.5 | 10.9 ± 1.0 | 2.9 ± 0.3 |
| C*) | 162.3 ± 26.4 | 12.0 ± 4.0 | 4.6 ± 0.4 |

*)Comparison example

Example 5

Preparation of Composites with Improved Mechanical Properties

The composite pastes based on bis-(2-vinyl-1,1-dicarboxylic acid monoethylester)resorcinylester (VCP 6) were prepared analogously to Example 4 (Table 3).

VCP-6

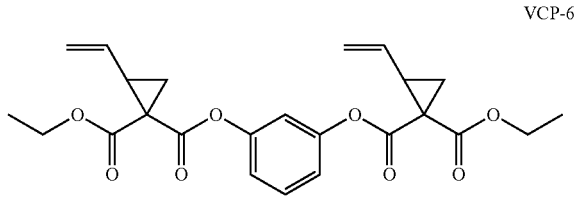 [SMILES: C=CC1CC1(C(=O)OCC)C(=O)Oc1cccc(OC(=O)C2(C(=O)OCC)CC2C=C)c1]

VCP 1, VCP 3 and VCP 4 were used as diluents. The results of the mechanical properties are reproduced in Table 4 and demonstrate that the highly reactive vinylcyclopropanes VCP 1 and VCP 3 (Composites D and E) lead to an improvement in the mechanical properties compared with the vinylcyclopropane VCP 4 (Composite F), which corresponds to the state of the art.

TABLE 3

Composition of the composites

| Component | Composite D (wt.-%) | Composite E (wt.-%) | Composite F*) (wt.-%) |
|---|---|---|---|
| VCP 1 | 5.22 | — | — |
| VCP 3 | — | 5.22 | — |
| VCP 4 | — | — | 5.22 |
| VCP 6 | 12.18 | 12.18 | 12.18 |
| Ivocerin ®[7] (Initiator) | 0.1 | 0.1 | 0.1 |
| EvoCeram ® Isofiller SDI[8] | 34.00 | 34.00 | 34.00 |

TABLE 3-continued

Composition of the composites

| Component | Composite D (wt.-%) | Composite E (wt.-%) | Composite F*) (wt.-%) |
|---|---|---|---|
| Barium-aluminium-borosilicate glass filler[3] | 33.50 | 33.50 | 33.50 |
| SiO$_2$—ZrO$_2$ Spherosil[4] | 10.00 | 10.00 | 10.00 |
| YbF$_3$[5] | 5.00 | 5.00 | 5.00 |

*)Comparison example
[3] Glass powder GM 27884, 1 μm, silanized (Schott)
[4] Tokoyama Soda
[5] Auer Remy
[7] Bis(4-methoxybenzoyl)diethylgermanium (Ivoclar Vivadent AG)
[8] Composite filler, weight-average particle size 30-40 μm (Ivoclar Vivadent AG)

TABLE 4

Mechanical properties of the composites

| Composite | Flexural strength (MPa) | Flexural modulus of elasticity (GPa) |
|---|---|---|
| D | 101.1 ± 5.2 | 8.2 ± 0.4 |
| E | 108.1 ± 3.7 | 8.5 ± 0.5 |
| F*) | 83.3 ± 9.1 | 6.3 ± 0.6 |

*)Comparison example

The invention claimed is:

1. Dental material which contains at least one vinylcyclopropane of the general formulae I,

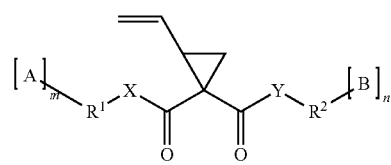

in which
A, B are COOH,
X, Y independently of each other are in each case O or NH,
R$^1$, R$^2$ independently of each other are in each case an aliphatic linear or branched C$_1$-C$_{10}$ hydrocarbon radical which can be interrupted by O, S or an ester group, an alicyclic or aromatic C$_6$-C$_{14}$ radical or an aromatic or non-aromatic heterocyclic radical which can contain 4 to 14 carbon atoms and 1 to 6 heteroatoms which are selected from N, O and/or S atoms, and
n, m independently of each other are in each case 0, 1 or 2,
wherein, if X=O and Y=O, then n+m≥1,
at least one further radically polymerizable monomer and
at least one initiator for the radical polymerization.

2. Dental material which contains 2 to 95 wt.-% vinylcyclopropane(s) according to claim 1, relative to the total mass of the material.

3. Dental material according to claim 2, which contains 5 to 85 wt.-% vinylcyclopropane(s).

4. Dental material according to claim 2, which contains 5 to 70 wt.-% vinylcyclopropane(s).

5. Dental material according to claim 2, which contains 10 to 50 wt.-% vinylcyclopropane(s).

6. Dental material according to claim 1, wherein the at least one further radically polymerizable monomer is selected from 1,1-di(ethoxycarbonyl)- or 1,1-di(methoxycarbonyl)-2-vinylcyclopropane, bis(2-vinylcyclopropane-1-carboxylic acid ethyl ester-1-carbonamido)-2,2-dimethyl-4-methylhexane, 1,8-bis(2-vinylcyclopropane-1-carboxylic acid ethyl ester-1-carbonyloxy)-3,6-dioxaoctane or the esters of 1-ethoxycarbonyl- or 1-methoxycarbonyl-2-vinylcyclopropanecarboxylic acid with ethylene glycol, 1,1,1-trimethylolpropane, 1,4-cyclohexanediol or resorcinol, bis-(2-vinyl-1,1-dicarboxylic acid monoethylester) resorcinylester, 2-(bicyclo[3.1.0]hex-1-yl)acrylic acid methyl or ethyl esters or disubstitution products thereof in the 3 position, (3,3-bis(ethoxycarbonyl)bicyclo[3.1.0]hex-1-yl)acrylic acid methyl or ethyl ester, or a mixture thereof.

7. Dental material according to claim 1, wherein the at least one further radically polymerizable is selected from methyl, ethyl, 2-hydroxyethyl, butyl, benzyl, tetrahydrofurfuryl or isobornyl (meth)acrylate, p-cumylphenoxyethylene glycol methacrylate (CMP-1E), bisphenol A di(meth)acrylate, bis-GMA (an addition product of methacrylic acid and bisphenol A diglycidyl ether), ethoxylated or propoxylated bisphenol A dimethacrylate, bisphenol A dimethacrylate 2-[4-(3-methacryloyloxyethoxyethyl)phenyl]-2-[4-(3-methacryloyloxyethyl)phenyl]-propane) (SR-348c) with 3 ethoxy groups, 2,2-bis[4-(2-(meth)acryloxypropoxy)phenyl]propane, UDMA (an addition product of 2-hydroxyethyl methacrylate (HEMA) and 2,2,4-trimethylhexamethylene diisocyanate), TMX-UDMA (an addition product of a mixture of HEMA and hydroxypropyl methacrylate (HPMA) with α,α,α',α'-tetramethyl-m-xylylene diisocyanate (TMXDI)), di-, tri- or tetraethylene glycol di(meth)acrylate, trimethylolpropane tri(meth)acrylate, pentaerythritol tetra(meth)acrylate, glycerol di- and trimethacrylate, 1,4-butanediol di(meth)acrylate, 1,10-decanediol di(meth)acrylate (D$_3$MA), 1,12-dodecanediol di(meth)acrylate and acid group-containing monomers, or a mixture thereof.

8. Dental material according to claim 1 which additionally contains at least one particulate filler.

9. Dental material according claim 1 which additionally contains at least one additive which is selected from solvents, water, ethanol or a mixture thereof, stabilizers, polymerization stabilizers, flavourings, dyes, microbiocidal active ingredients, fluoride-ion-releasing additives, optical brighteners, plasticizers and/or UV-absorbers.

10. Dental material according claim 1 which contains
a) 2 to 95 wt.-% of the at least one vinylcyclopropane of general formula I,
b) 0.01 to 5 wt.-% of the at least one initiator for the radical polymerization,
c) greater than 0 and up to 80 wt.-% of the at least one further radically polymerizable monomer and optionally
d) 0 to 85 wt.-% filler(s),
in each case relative to the total mass of the material.

11. Dental material according claim 1 which contains
a) 2 to 90 wt.-% of the at least one vinylcyclopropane of general formula I,
b) 0.1 to 3.0 wt.-% of the at least one initiator for the radical polymerization,
c) greater than 0 and up to 60 wt.-% of the at least one further radically polymerizable monomer and optionally
d) 0 to 80 wt.-% filler(s),
in each case relative to the total mass of the material.

12. Dental material according claim 1 which contains
a) 10 to 85 wt.-% of the at least one vinylcyclopropane of general formula I,
b) 0.2 to 2 wt.-% of the at least one initiator for the radical polymerization,
c) greater than 0 and up to 50 wt.-% of the at least one further radically polymerizable monomer and optionally
d) 0 to 80 wt.-% filler(s),
in each case relative to the total mass of the material.

13. Dental material according to claim 10 which contains 0 to 40 wt.-% filler(s), for use as coating material, or which contains 10-70 wt.-% filler(s), for use as cement, or which contains 10-85 wt.-% filler(s), for use as filling material.

14. Dental material according to claim 13 for use as filling material which contains
a) 2 to 50 wt.-% of the at least one vinylcyclopropane of general formula I,
b) 0.1 to 3 wt.-% of the at least one initiator or 0.1 to 3 wt.-% of the at least one initiator being a photoinitiator for the radical polymerization,
c) greater than 0 and up to to 50 wt.-% of the at least one further radically polymerizable monomer, and
d) 40 to 85 wt.-% filler(s),
in each case relative to the total mass of the material.

15. Dental material according to claim 13 for use as filling material which contains
a) 5 to 50 wt.-% of the at least one vinylcyclopropane of general formula I,
b) 0.2 to 3.0 wt.-% of the at least one initiator for the radical polymerization,
c) greater than 0 and up to 40 wt.-% of the at least one further radically polymerizable monomer, and
d) 40 to 80 wt.-% filler(s),
in each case relative to the total mass of the material.

16. Dental material according to claim 13 for use as filling material which contains
a) 10 to 50 wt.-% of the at least one vinylcyclopropane of general formula I,
b) 0.2 to 1 wt.-% of the at least one initiator for the radical polymerization,
c) greater than 0 and up to 30 wt.-% of the at least one further radically polymerizable monomer, and
d) 40 to 80 wt.-% filler(s),
in each case relative to the total mass of the material.

17. Method of using the dental material according to claim 1 for the production or repair of dental restorations, prostheses, artificial teeth, inlays, onlays, crowns or bridges.

18. Method of using the dental material according to claim 1 for the production of a shaped body by a stereolithographic process.

19. Method of using at least one vinylcyclopropane of the general formulae I,

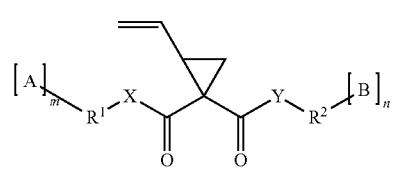

in which
A, B are COOH,
X, Y independently of each other are in each case 0 or NH, $R^1$, $R^2$ independently of each other are in each case an aliphatic linear or branched $C_1$-$C_{10}$ hydrocarbon radical which can be interrupted by O, S or an ester group, an alicyclic or aromatic $C_6$-$C_{14}$ radical or an aromatic or non-aromatic heterocyclic radical which can contain 4 to 14 carbon atoms and 1 to 6 heteroatoms which are selected from N, O and/or S atoms, and n, m independently of each other are in each case 0, 1 or 2, wherein, if X=O and Y=O, then n+m≥1 at least one further radically polymerizable monomer and at least one initiator for the radical polymerization for the preparation of a dental material.

20. Dental material according to claim 12, wherein the at least one initiator for the radical polymerization is a photoinitiator.

* * * * *